(12) United States Patent
Williams

(10) Patent No.: US 11,510,726 B2
(45) Date of Patent: Nov. 29, 2022

(54) BIPOLAR ELECTROSURGICAL INSTRUMENTS

(71) Applicant: GYRUS MEDICAL LIMITED, Cardiff (GB)

(72) Inventor: Wayne Williams, Penarth (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 902 days.

(21) Appl. No.: 16/248,965

(22) Filed: Jan. 16, 2019

(65) Prior Publication Data

US 2019/0216533 A1    Jul. 18, 2019

(30) Foreign Application Priority Data

Jan. 17, 2018 (GB) ...................................... 1800727

(51) Int. Cl.
*A61B 18/12* (2006.01)
*A61B 18/14* (2006.01)
(Continued)

(52) U.S. Cl.
CPC ...... *A61B 18/1445* (2013.01); *A61B 18/1206* (2013.01); *A61B 2017/2925* (2013.01);
(Continued)

(58) Field of Classification Search
CPC ............ A61B 18/1206; A61B 18/1445; A61B 2018/00095; A61B 2018/0063;
(Continued)

(56) References Cited

U.S. PATENT DOCUMENTS 4,200,104 A * 4/1980 Harris .................... A61B 18/16
607/152
2002/0115997 A1* 8/2002 Truckai .............. A61B 18/1445
606/51
(Continued)

FOREIGN PATENT DOCUMENTS

DE           9422383 U1      3/2001
DE           10351818 A1     6/2005
(Continued)

OTHER PUBLICATIONS

Jun. 25, 2018 Search Report issued in British Patent Application No. 1800727.8.
(Continued)

*Primary Examiner* — Daniel W Fowler
(74) *Attorney, Agent, or Firm* — Oliff PLC

(57) ABSTRACT

A bipolar surgical instrument (1) comprises a body (2), first and second opposed jaws (18, 20) located at the distal end of a shaft (10), the first jaw (18) being movable with respect to the second jaw (20) between an open position in which the first and second jaws (18, 20) are spaced apart from one another, and a closed position in which the first and second jaws (18, 20) are adjacent one another. The first and second elongate jaw members (18, 20) have respective first and second electrodes. A power cable having a pair of electrically conductive elements, is provided to connect a source of radio frequency electromagnetic energy to the first and second electrodes. A capacitive element is located in the instrument, and is connected in series between a first one of the pair of electrically conductive elements of the cable and the first electrode.

7 Claims, 5 Drawing Sheets

(51) Int. Cl.
*A61B 18/00* (2006.01)
*A61B 17/29* (2006.01)

(52) U.S. Cl.
CPC .............. *A61B 2018/0063* (2013.01); *A61B 2018/00095* (2013.01); *A61B 2018/126* (2013.01); *A61B 2018/128* (2013.01); *A61B 2018/1286* (2013.01)

(58) Field of Classification Search
CPC ........ A61B 2018/126; A61B 2018/128; A61B 2018/1286
See application file for complete search history.

(56) References Cited

U.S. PATENT DOCUMENTS

| | | | |
|---|---|---|---|
| 2003/0009164 A1* | 1/2003 | Woloszko | A61B 18/149 606/49 |
| 2005/0096681 A1 | 5/2005 | Desinger et al. | |
| 2005/0177150 A1* | 8/2005 | Amoah | A61B 18/1206 606/45 |
| 2008/0249523 A1* | 10/2008 | McPherson | A61B 18/1445 606/41 |
| 2008/0281316 A1 | 11/2008 | Carlton et al. | |
| 2011/0077642 A1 | 3/2011 | Farin | |
| 2011/0140607 A1* | 6/2011 | Moore | H05H 1/36 315/111.21 |
| 2011/0245826 A1* | 10/2011 | Woloszko | A61B 18/1206 606/41 |
| 2012/0071712 A1* | 3/2012 | Manwaring | A61B 18/10 600/104 |
| 2016/0066980 A1 | 3/2016 | Schall et al. | |
| 2017/0311975 A1 | 11/2017 | Atwell | |

FOREIGN PATENT DOCUMENTS

| | | |
|---|---|---|
| EP | 2057954 A1 | 5/2009 |
| WO | 2009/080273 A1 | 7/2009 |

OTHER PUBLICATIONS

Nov. 27, 2019 Office Action issued in German Patent Application No. 102019100653.8.

* cited by examiner

BIPOLAR ELECTROSURGICAL INSTRUMENTS

BACKGROUND OF THE INVENTION

Bipolar surgical instruments are used to clamp and seal tissue, such as blood vessels, during surgical procedures. Clamping is typically achieved using a pair of opposed jaws that are remotely operable to clamp around the vessel being sealed. Sealing is typically achieved using application of radio frequency energy delivered to the tissue being sealed by electrodes mounted on the opposed jaws of the instrument.

Existing designs of such instruments may not provide optimal transfer of electrical power to the tissue, and so may not provide optimal tissue sealing. It is, therefore, desirable to provide an improved bipolar surgical instrument that, at least partially, addresses these drawbacks.

SUMMARY OF THE INVENTION

Aspects of the present invention are set out in the attached claims.

According to one exemplary aspect, there is provided a bipolar electrosurgical instrument comprising a body; an elongate shaft attached to the body, the elongate shaft extending to a distal end; first and second elongate jaw members located at the distal end of the elongate shaft, and carrying respective first and second electrodes, the jaw members being movable relative to one another between an open position in which the first and second electrodes are spaced apart from one another, and a closed position in which the first electrode is adjacent the second electrode; a power cable having a pair of electrically conductive elements, and having a first end for connection with a source of radio frequency electromagnetic energy, and a second end for connection to the first and second electrodes; and a first capacitive element located in the instrument, and connected in series between a first one of the pair of electrically conductive elements of the cable and the first electrode.

One example further comprises a second capacitive element located in the instrument and connected in series between a second one of the pair of electrically conductive elements, and the second electrode.

In one example, the first electrode is an active electrode and the second electrode is a return electrode. In an alternative example, the first electrode is a return electrode and the second electrode is an active electrode.

The or each capacitive element may be a capacitor.

One example further comprises a control cable including at least one control conductor for providing a control signal path. One example further comprises a measurement cable including at least one measurement conductor for providing a measurement signal path.

According to another exemplary aspect, there is provided an electrosurgical system comprising a bipolar electrosurgical instrument according to the first exemplary aspect, and a waveform generator connected with the power cable of the instrument and operable to supply radio frequency signals to the first and second electrodes via the power cable.

In one example, the waveform generator comprises a radio frequency signal generator operable to supply a radio frequency signal to the first and second electrodes via the power cable, and a controller operable to control operation of the radio frequency signal generator, in dependence upon a received control input.

DETAILED DESCRIPTION OF THE PREFERRED EMBODIMENTS

Figure 1:
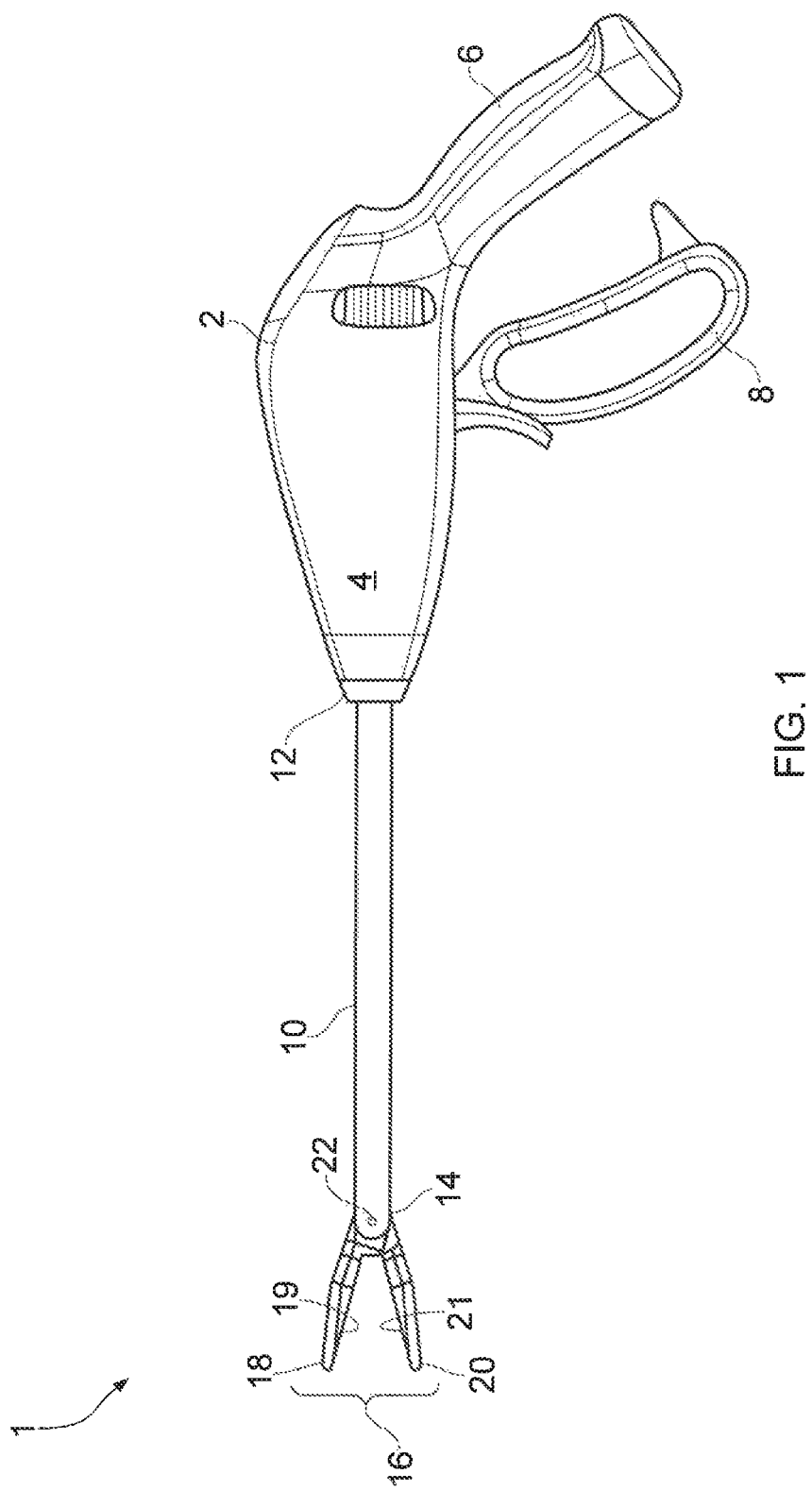
FIGS. 1 and 2 show side views of a bipolar surgical instrument embodying one aspect of the present invention in open and closed positions respectively.
Figure 2:
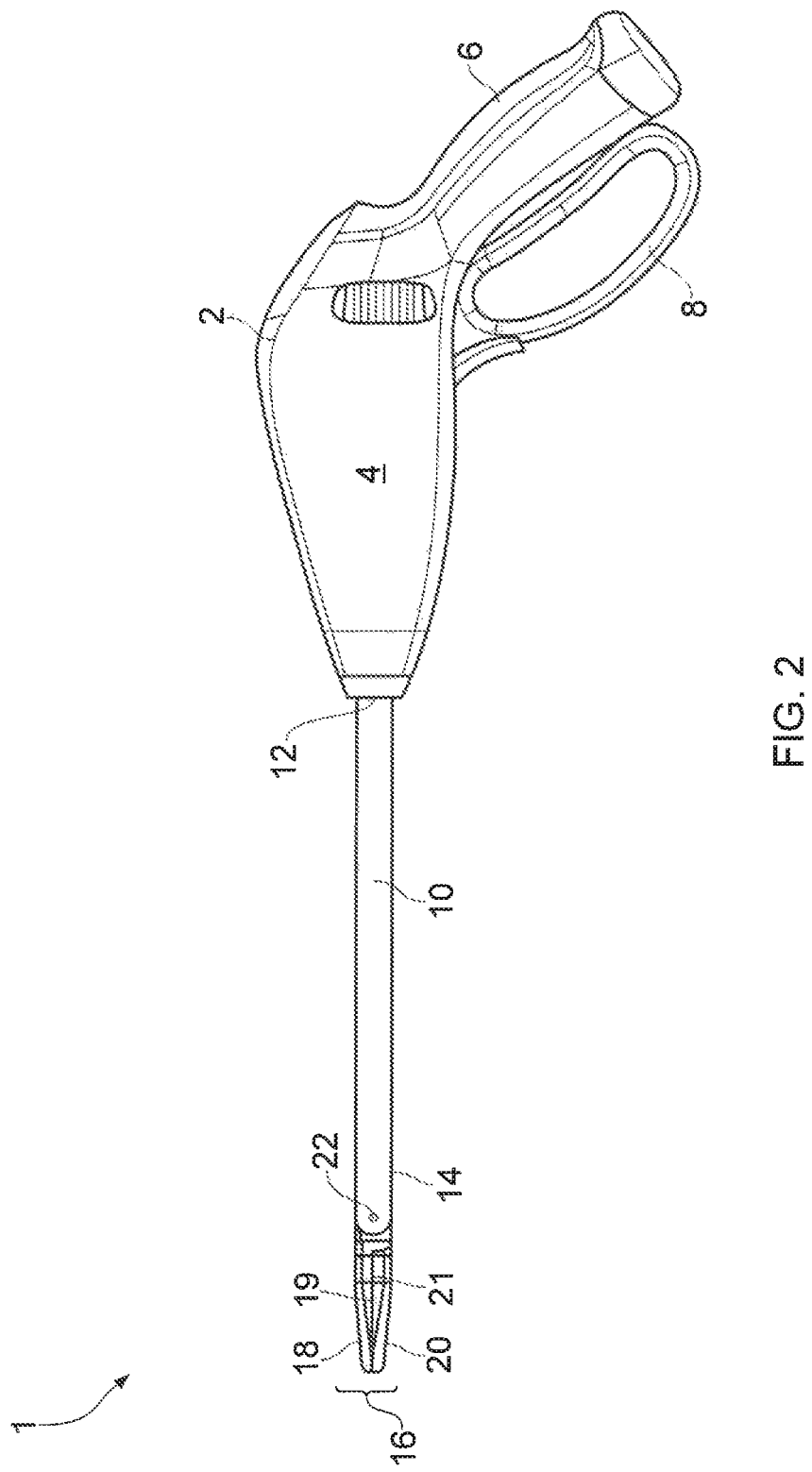

An example bipolar surgical instrument 1 is shown schematically in FIGS. 1 and 2. FIG. 1 illustrates an open position of the instrument 1, and FIG. 2 illustrates a closed position thereof.

The instrument 1 comprises a body 2 having a main housing 4 from which a fixed grip 6 extends. The fixed grip 6 is held during use by the operator of the instrument 1. A movable actuation grip 8 is movably mounted on the main housing 4 of the body 2. An elongate shaft 10 is attached to the main housing 4 of the body 2, and extends from a proximal end 12 at the main housing 4, to a distal end 14 of the shaft 10. The shaft 10 defines a longitudinal axis therealong, and an elongate passage extends from the proximal end 12 to the distal end 14 of the shaft 10.

A pair 16 of opposed jaws are located at the distal end 14 of the shaft 10. The pair 16 of jaws comprises a first jaw 18 and a second jaw 20. In the example of FIGS. 1 and 2, the first and second jaws 18 and 20 are pivotally mounted on a jaw pivot 22. The first and second jaws 18 and 20 are pivotable about the jaw pivot 22, between an open position (as shown in FIG. 1) in which the jaws 18 and 20 are separated from one another, and a closed position (as shown in FIG. 2) in which the jaws 18 and 20 are adjacent one another. In another example of a bipolar instrument embodying the present invention, only one of the jaws is movable. In another example, the movable jaw or jaws may be movable in any suitable manner, for example linearly, or in a combination of rotation and linear movement. The exact nature of the movement of the jaws is not important in the context of the present invention.

The first and second jaws 18 and 20 carry first and second electrodes 19 and 21 respectively. The first and second electrodes 19 and 21 are arranged to apply radio frequency electromagnetic energy to tissue held between the first and second jaws 18 and 20.

In use, the operator of the instrument 1 moves the actuation grip 8 from a first position (shown in FIG. 1) to a second position (shown in FIG. 2) in order to move the jaws 18 and 20 from the open position to the closed position. During an operation, tissue to be sealed is held between the jaws 18 and 20 in the closed position for a predetermined time period, with pressure applied by the operator, and with radio frequency energy applied to the tissue. The radio frequency energy serves to seal the held tissue.

Figure 3:
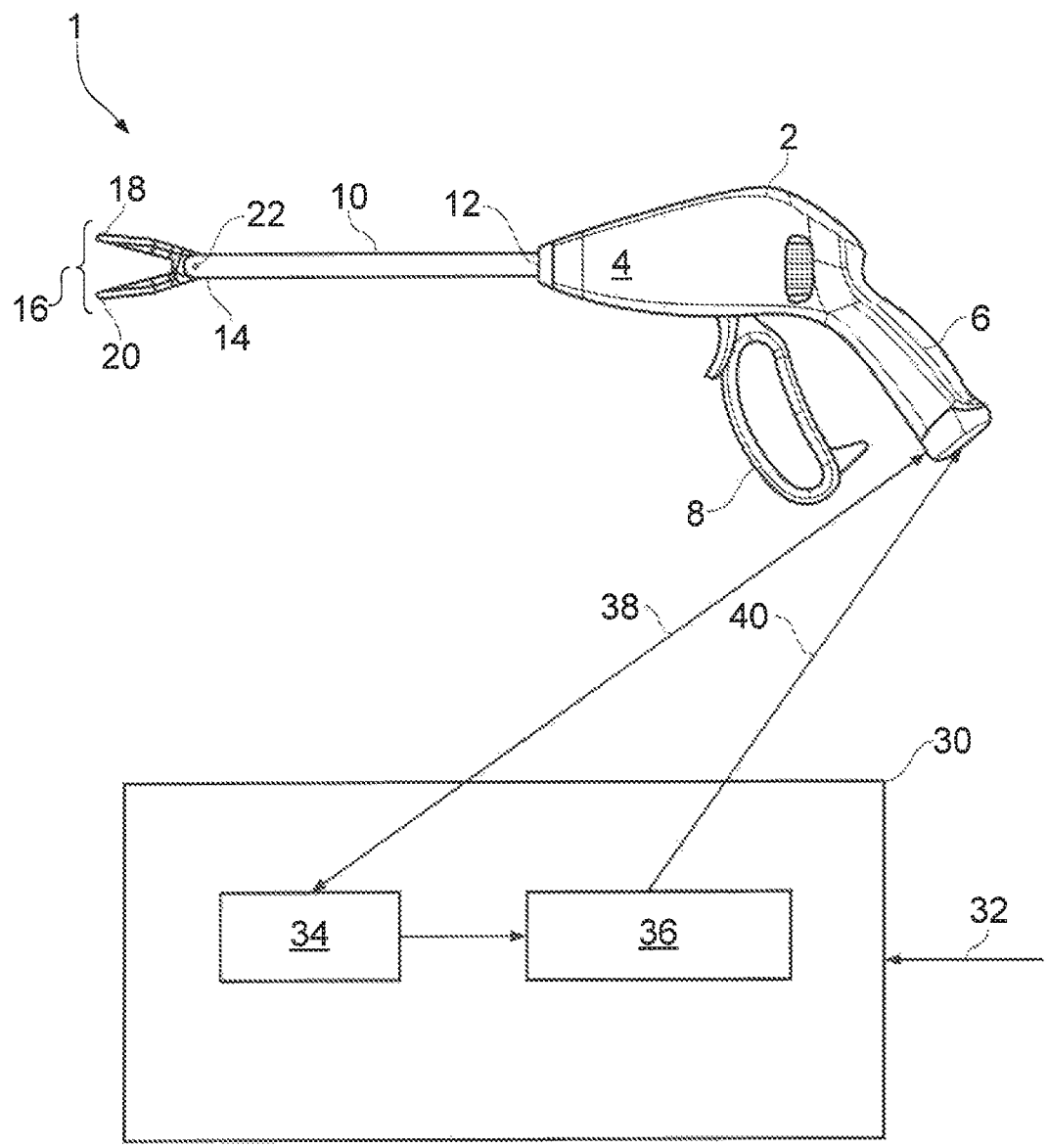
FIG. 3 illustrates a controller for use with a bipolar surgical instrument.

FIG. 3 illustrates the instrument 1 connected with a waveform generator 30. The waveform generator 30 receives an electrical power supply 32, and includes a controller 34 and a radio frequency signal generator 36. A control cable 38 connects the controller 34 to control inputs located, in one example, in or on the instrument 1. The control inputs may be located separately from the instrument 1, for example as a foot switch. A measurement cable may also be provided to provide a path for measurement signals.

The controller 34 is operable to control the signal generator 36 which is connected by power cable 40 to the instrument 1. The power cable 40 includes a pair of conductors that are connected to respective ones of the first and second electrodes 19 and 21 of the instrument 1. Upon reception of an appropriate control signal, the controller 34 causes the signal generator 36 to supply a radio frequency electrical output signal via the power cable 40 to the first and second electrodes 19 and 21. One of the electrodes is defined as the active electrode and one as the return electrode.

The output radio frequency electrical signal may have any appropriate characteristics such as voltage, current, and frequency, and may be generated to apply a desired sealing waveform to the tissue being held between the first and second jaws 18 and 20.

Figure 4:
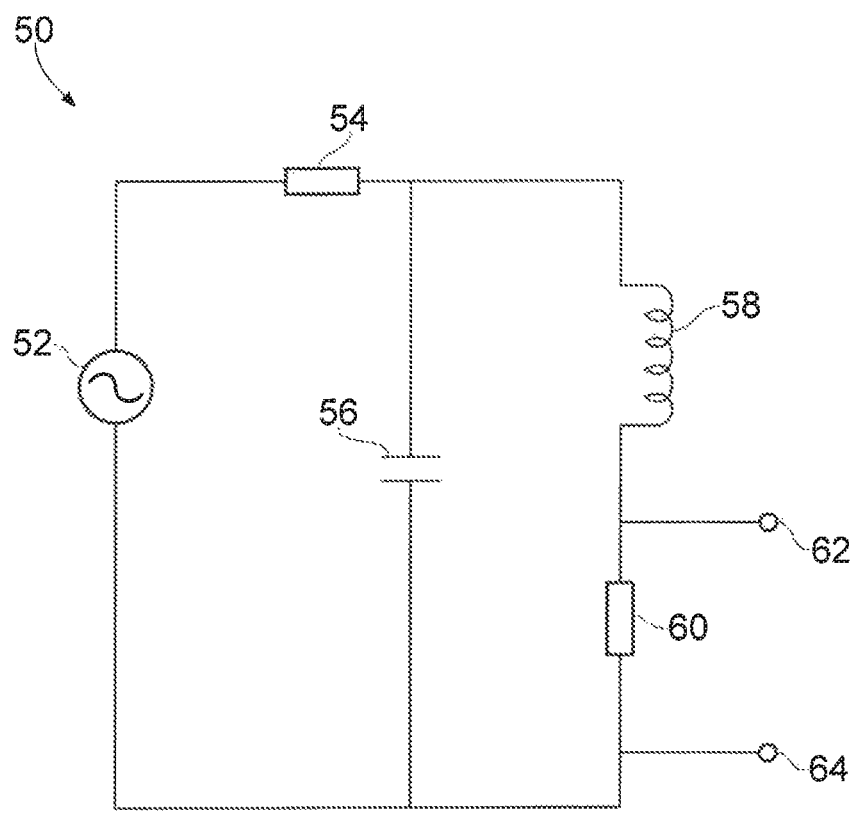
FIG. 4 illustrates an electrical model of a bipolar surgical instrument.

FIG. 4 illustrates an electrical model 50 of a previously-considered instrument and signal generator connected as in FIG. 3. The signal generator 52 is connected to supply radio frequency signals to the first and second electrodes 62 and 64 of the instrument, via the power cable. The power cable has electrical characteristics represented by resistance 54, capacitance 56 and inductance 58. The tissue being sealed has an impedance, and this is represented by element 60 in FIG. 4.

It will be readily appreciated that the electrical characteristics of the system depend largely on the frequency of the radio frequency signal being supplied by the signal generator, and on the impedance presented by the tissue being sealed. At suitable frequencies of radio frequency signal to achieve the required sealing, the inductance 58 of the cable can result in significant voltage drop across the length of the cable. This voltage drop results in the voltage applied across the first and second electrodes 19 and 21 being significantly reduced, which results in poor energy transfer to the tissue being sealed. This is particularly noticeable when low tissue impedance is encountered, for example of the order of 50 Ohms.

Figure 5:
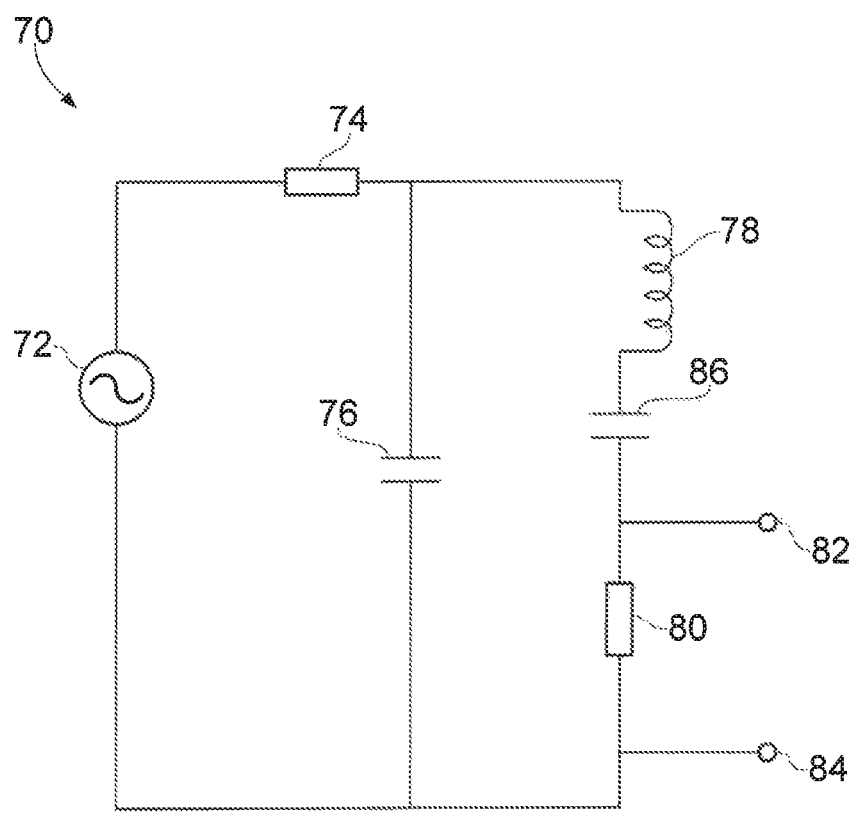
FIG. 5 illustrates an electrical model of a bipolar surgical instrument embodying the present invention.

FIG. 5 illustrates an electrical model 70 of an instrument and signal generator embodying an aspect of the present invention, as connected as in FIG. 3. The signal generator 72 is connected to supply radio frequency signals to the first and second electrodes 82 and 84 of the instrument, via the power cable. Once again, the power cable has electrical characteristics represented by resistance 74, capacitance 76 and inductance 78. The tissue being sealed has an impedance, and this is represented by element 80 in FIG. 5. In accordance with the principles of the present invention, a capacitive element 86, for example a capacitor, is connected in series between a first one of the pair of electrically conductive elements of the cable and the first electrode 19. The capacitive element 86 is located within the instrument 1, either in the body of the instrument 1, or in the elongate shaft 10 thereof.

The capacitance value of the capacitive element 86 is chosen so as to resonate with the cable inductance 78 at the frequency of signal appropriate for use with low impedance loads. The capacitance value of the capacitive element 86 may be calculated according to the following formula:

$$C = \frac{1}{(2\pi F_r)^2 \times L}$$

where C is the capacitance, $F_r$ is the operating frequency of the system, and L is the cable inductance 78.

The capacitive element 86 may be located in series between either one of the pair of electrically conductive elements of the cable and either one of the first and second electrodes. Alternatively, the capacitive element 86 mat be provided by two elements, one connected in series between a first one of the pair of electrically conductive elements of the cable and the first electrode, and one element connected in series between the other one of the pair of electrically conductive elements, and the second electrode.

In such a manner, an embodiment of the present invention is able to provide improved tissue sealing characteristics for a bipolar electrosurgical instrument.

The invention claimed is:

1. A bipolar electrosurgical instrument comprising:
a body;
an elongate shaft (i) attached to the body and (ii) having a distal end;
first and second elongate jaw members at the distal end of the elongate shaft, the first elongate jaw member carrying a first electrode that is an active electrode and the second elongate jaw member carrying a second electrode that is a return electrode, the elongate jaw members being movable relative to one another between an open position in which the first and second electrodes are spaced apart from one another and a closed position in which the first electrode is adjacent the second electrode to clamp and seal tissue engaged between the first electrode and the second electrode;
a power cable having (i) a pair of electrically conductive elements, (ii) a first end for connection with a source of radio frequency electromagnetic energy and (iii) a second end for connection to the first and second electrodes;
a first capacitive element connected in series between a first one of the pair of electrically conductive elements of the cable and the first electrode; and
a second capacitive element connected in series between a second one of the pair of electrically conductive elements and the second electrode,
wherein the first capacitive element and the second capacitive element are configured such that a capacitance value of each of the first capacitive element and the second capacitive element resonates with inductance of the power cable at low impedance loads.

2. A bipolar electrosurgical instrument as claimed in claim 1, wherein each of the first capacitive element and the second capacitive element is a capacitor.

3. A bipolar electrosurgical instrument as claimed in claim 1, further comprising a control cable including at least one control conductor for providing a control signal path.

4. A bipolar electrosurgical instrument as claimed in claim 1, further comprising a measurement cable including at least one measurement conductor for providing a measurement signal path.

5. An electrosurgical system comprising a bipolar electrosurgical instrument as claimed in claim 1, and a waveform generator connected with the power cable that is the source of the radio frequency electromagnetic energy and operable to supply radio frequency signals to the first and second electrodes via the power cable.

6. An electrosurgical system as claimed in claim 5, wherein the waveform generator comprises a radio frequency signal generator operable to supply a radio frequency signal to the first and second electrodes via the power cable, and a controller operable to control operation of the radio frequency signal generator, in dependence upon a received control input.

7. A bipolar electrosurgical instrument as claimed in claim 1, wherein the capacitance value of each of the first capacitive element and the second capacitive element is calculated by this formula:

$$C = \frac{1}{(2\pi F_r)^2 \times L}$$

where C is the capacitance, $F_r$ is the operating frequency of the system, and L is the cable inductance.

\* \* \* \* \*